United States Patent
Kuchenbeiser et al.

(10) Patent No.: US 9,701,695 B1
(45) Date of Patent: Jul. 11, 2017

(54) SYNTHESIS METHODS FOR AMINO(HALO)SILANES

(71) Applicant: American Air Liquide, Inc., Fremont, CA (US)

(72) Inventors: Glenn Kuchenbeiser, Newark, DE (US); Venkateswara R. Pallem, Hockessin, DE (US); Guillaume Husson, Newark, DE (US)

(73) Assignee: American Air Liquide, Inc., Fremont, CA (US)

( * ) Notice: Subject to any disclaimer, the term of this patent is extended or adjusted under 35 U.S.C. 154(b) by 0 days.

(21) Appl. No.: 14/985,006

(22) Filed: Dec. 30, 2015

(51) Int. Cl.
    *C07F 7/02* (2006.01)
    *C07F 7/12* (2006.01)

(52) U.S. Cl.
    CPC .............. *C07F 7/025* (2013.01); *C07F 7/123* (2013.01); *C07F 7/12* (2013.01)

(58) Field of Classification Search
    CPC .................................. C07F 7/123; C07F 7/12
    USPC .................... 556/477, 466, 467, 468, 407
    See application file for complete search history.

(56) References Cited

U.S. PATENT DOCUMENTS

| | | | |
|---|---|---|---|
| 7,125,582 B2 | 10/2006 | McSwiney et al. | |
| 7,402,243 B2 * | 7/2008 | Liu | B01J 20/286 210/198.2 |
| 9,233,990 B2 * | 1/2016 | Xiao | C07F 7/025 |
| 2012/0021127 A1 | 1/2012 | Sato et al. | |
| 2012/0277457 A1 | 11/2012 | Lehmann et al. | |
| 2013/0078392 A1 | 3/2013 | Xiao et al. | |
| 2013/0319290 A1 | 12/2013 | Xiao et al. | |
| 2013/0323435 A1 | 12/2013 | Xiao et al. | |
| 2014/0051264 A1 | 2/2014 | Mallick et al. | |
| 2014/0273477 A1 | 9/2014 | Niskanen et al. | |
| 2014/0273528 A1 | 9/2014 | Niskanen et al. | |
| 2014/0273531 A1 | 9/2014 | Niskanen et al. | |

FOREIGN PATENT DOCUMENTS

| | | |
|---|---|---|
| JP | 2006 096675 | 4/2006 |
| WO | WO 2006 059187 | 6/2006 |
| WO | WO 2009 087609 | 7/2009 |
| WO | WO 2011 123792 | 10/2011 |
| WO | WO 2012 167060 | 12/2012 |

OTHER PUBLICATIONS

Anderson, D.G. et al., "Preparations, properties, and vibrational spectra of some (dimethylamino)halogenosilanes," J. Chem. Soc. Dalton Trans. 1987, 3029-3034.

Cass, R. et al., "438. Dimethylaminochlorosilanes," J. Chem. Soc., 1952, 2347-2349.

Emsley, J., "Aminosilane-iodosilane adducts," J. Chem. Soc. (A), 1968, 1009-1012.

Hassler, K. et al., "Synthese und Kernresonanzspektren von Bromdisilanen und Iodisilanen," J. Organometallic Chem., 398 (1990) 225-227 and English Abstract.

Passarelli, V. et al., "Aminolysis of the Si-Cl bond and ligand exchange reaction between silicon amido derivatives and $SiCl_4$: synthetic applications and kinetic investigations," Dalton Transl 2003, 413-419.

Schott, G. et al., "Kurze Originalmitteilungen. Über Dimethylamino-brom-silane," Z. Chem. 1 Jg., Heft 4, 1961, 123.

Stüger, H. et al., "Aminochlorodisilanes: precursors to multifuncionalized disilane derivatives," J. Organometallic Chem., 547 (1997) 227-233.

* cited by examiner

*Primary Examiner* — Elvis O Price
(74) *Attorney, Agent, or Firm* — Patricia E. McQueeney

(57) ABSTRACT

Disclosed are methods of synthesizing an amino(halo)silane comprising the step of reacting a halosilane having the formula $Si_aH_bX_c$ with an aminosilane having the formula $Si_dH_e(NR^1R^2)_f$ to produce the amino(halo)silane having the formula $Si_wH_xX_y(NR^1R^2)_z$, wherein X=Br or I; each $R^1$ and $R^2$ is independently selected from a $C_1$-$C_{10}$ alkyl, aryl, or hetero group; a, d, and w independently=1 to 4; b+c=2a+2; b=1 to 2a+1; c=1 to 2a+1; e+f=2d+2; e=1 to 2d+1; f=1 to 2d+1; x+y+z=2w+2; and $R^1$ and $R^2$ may be joined to form a nitrogen-containing heterocycle.

20 Claims, 3 Drawing Sheets

SYNTHESIS METHODS FOR AMINO(HALO)SILANES

TECHNICAL FIELD

Disclosed are methods of synthesizing an aminohalosilane comprising the step of reacting a halosilane having the formula $Si_aH_bX_c$ with an aminosilane having the formula $Si_dH_e(NR^1R^2)_f$ to produce the aminohalosilane having the formula $Si_wH_xX_y(NR^1R^2)_z$, wherein X=Br or I; each $R^1$ and $R^2$ is independently selected from a $C_1$-$C_{10}$ alkyl, aryl, or hetero group; a, d, and w independently=1 to 4; b+c=2a+2; b=1 to 2a+1; c=1 to 2a+1; e+f=2d+2; e=1 to 2d+1; f=1 to 2d+1; x+y+z=2w+2; x=1 to 2w; y=1 to 2w; z=1 to 2w; and $R^1$ and $R^2$ may be joined to form a nitrogen-containing heterocycle.

BACKGROUND

Amino(halo)silanes are attracting attention owing to their chemical properties and potential usage as film deposition precursors across a wide range of industries. The deposited films may be useful as semiconductor dielectric materials and coatings, photovoltaic device coatings, refractory optical coatings and aerospace materials.

Synthesis of amino(halo)silanes has been achieved via aminolysis of halosilanes (J. Chem. Soc. 1952, pp. 2347-2349). The synthesis also produces ammonium halide salt byproducts.

US2012/0277457 to Lehmann et al. discloses methods of making aminosilanes as well as intermediate compounds such as haloaminosilane compounds. The haloaminosilane compounds are made by reacting a halosilane having the formula $H_nSiX_{4-n}$, wherein n is 0, 1, or 2 and X is Cl, Br, or a mixture of Cl and Br, and an amine to provide the haloaminosilane compound.

US2013/0078392 to Xiao et al. discloses halogenated amino(halo)silane precursors having the formula $X_mR^1{}_nH_pSi(NR^2R^3)_{4-m-n-p}$ where X is Cl, Br and I. The precursors are synthesized by reacting dichlorosilane or trichlorosilane with a secondary amine (i.e., $HNR_2$ or 2,2-dimethylpiperidine) or Li amine (Li—$NR_2$ or Li-2,2-dimethylpiperidine) in an organic solvent or solvent mixture and using a tertiary amine (i.e., $NR_3$) to absorb the hydrogen chloride byproduct.

Xiao et al. disclose another family of Si-containing precursors in US2013/0323435 which have the formula $(R^1R^2N)_n$—$SiH_{3-n}SiH_3$ wherein $R^1$ is selected from linear or branched C3 to C10 alkyl group, linear or branched C3 to C10 alkenyl group, linear or branched C3 to C10 alkynyl group, C1 to C6 dialkylamino group, electron withdrawing group, and C6 to C10 aryl group; $R^2$ is selected from hydrogen, linear or branched C1 to C10 alkyl group, linear or branched C3 to C6 alkenyl group, linear or branched C3 to C6 alkynyl group, C1 to C6 dialkylamino group, C6 to C10 aryl group, linear or branched C1 to C6 fluorinated alkyl group, electron withdrawing group, and C4 to C10 aryl group; optionally wherein $R^1$ and $R^2$ are linked together to form ring selected from substituted or unsubstituted aromatic ring or substituted or unsubstituted aliphatic ring; and n=1 or 2. The Si-containing precursors are synthesized by reacting a monohalodisilane or lower molecular dialkylaminodisilane with an amine in an organic solvent or solvent mixture.

Additionally, Xiao et al also disclose another family of Si-containing precursors in US2013/0319290 which have the formula $(R^1R^2N)$—$SiH_2SiH_2$—$(NR^3R^4)$ and methods for forming silicon-containing films and wherein $R^1$ and $R^3$ are independently selected from linear or branched C3 to C10 alkyl group, a linear or branched C3 to C10 alkenyl group, a linear or branched C3 to C10 alkynyl group, a C1 to C6 dialkylamino group, an electron withdrawing and a C6 to C10 aryl group; $R^2$ and $R^4$ are independently selected from hydrogen, a linear or branched C3 to C10 alkyl group, a linear or branched C3 to C10 alkenyl group, a linear or branched C3 to C10 alkynyl group, a C1 to C6 dialkylamino group, an electron withdrawing, and a C6 to C10 aryl group; and wherein any one, all, or none of $R^1$ and $R^2$, $R^3$ and $R^4$, $R^1$ and $R^3$, or $R^2$ and $R^4$ are linked to form a ring. The Si-containing precursors are synthesized by reacting a dichlorodisilane with an amine in an organic solvent or solvent mixture.

Harald Stüger et al. disclose synthesis of multifunctionalized disilane derivatives from bis(trimethylsilyl)aminopentachlorodisilane, 1,2-bis[bis(trimethylsilyl)amino]tetrachlorodisilane, or bis(phenyldimethylsilyl)aminopentachlorodisilane by reacting $Si_2Cl_6$ with $LiN(SiMe_3)_2$ or $LiN(SiMe_2Ph)_2$. (J. Organometallic Chem., 547 (1997), pp. 227-233).

Another published synthetic route utilizes protonation of aminosilanes using a haloacid ('Preparations, Properties, and Vibrational Spectra of some (dimethylamino)halogenosilanes,' Anderson et al., *J. Chem Soc. Dalt. Trans.*, 1987, 3029-3034). The synthesis also produces ammonium halide salt byproducts.

Disilane containing precursors bearing both alkyl and amino groups have been disclosed for deposition of SiCN thin films by Tsukada and Dussarrat in JP 2006096675. A phenyl-substituted disilane is reacted with HCl, wherein the Cl replaces the phenyl to produce a chlorodisilane. The resulting chlorodisilane is reacted with an alkali amine (i.e., $LiNMe_2$) to produce the amino-substituted disilane product.

Passarelli et al. ('Aminolysis of the Si—Cl bond and ligand exchange reaction between silicon amido derivatives and $SiCl_4$: synthetic applications and kinetic investigations, '*Dalt. Trans.,* 2003, 413-419) have shown the utility of synthesis of amino(chloro)silanes using a ligand exchange route wherein an aminosilane $SiCl_n(NR_2)_{4-n}$ is reacted with a chlorosilane $SiCl_4$ in the appropriate ratio to produce the targeted products without the formation of ammonium halide salt byproducts.

A need remains for synthesis methods to produce bromo- and iodo-aminosilicon precursors that may be suitable for use in film deposition processes.

SUMMARY

Methods of synthesizing aminohalosilane precursors are disclosed. The methods comprise the step of reacting a halosilane having the formula $$Si_aH_bX_c$$

with an aminosilane having the formula $$Si_dH_e(NR^1R^2)_f$$

to produce the aminohalosilane reaction product having the formula:

$$Si_wH_xX_y(NR^1R^2)_z$$

wherein X=Br or I; each $R^1$ and $R^2$ independently selected from a $C_1$-$C_{10}$ alkyl, aryl, or hetero group; a, d, and w=1 to 4; b+c=2a+2; b=1 to 2a+1; c=1 to 2a+1; e+f=2d+2; e=1 to 2d+1; f=1 to 2d+1; x+y+z=2w+2; x=1 to 2w; y=1 to 2w; z=1 to 2w; and $R^1$ and $R^2$ may be joined to form a nitrogen-containing heterocycle. The disclosed methods may include one or more of the following aspects:

X=I;
X=Br;
$R^1$ being Me, Et, Pr, or Bu;
$R^2$ being Me, Et, Pr, or Bu;
$NR^1R^2$ forming morpholino, thiomorpholino, or piperazine;
$NR^1R^2$ forming imidazole;
b=e;
b≠e;
a=d=w and b=e;
the method producing a single aminohalosilane reaction product;
when a=1 and c=4, X is not I;
a=1;
a=2;
c=2;
c=3;
d=1;
d=2;
f=2;
f=3;
further comprising adding a solvent;
the solvent being toluene, THF, benzene, diethyl ether, pentane, hexane, anisole, or digylme;
the solvent being toluene, THF, diethyl ether, pentane, anisole, or diglyme;
the solvent being toluene;
the solvent being THF;
the solvent being diethyl ether;
the solvent being anisole;
the solvent being diglyme;
not including a solvent;
performing the method neat;
performing the method under an inert atmosphere;
the inert atmosphere being Ar, $N_2$, He, or Kr;
the inert atmosphere being Ar;
the inert atmosphere being $N_2$;
performing the method at a temperature ranging from approximately −100° C. to approximately 100° C.;
performing the method at a temperature ranging from approximately −78° C. to approximately −60° C.;
performing the method at a temperature ranging from approximately 0° C. to approximately 23° C.;
further comprising removing solid byproducts from the crude reaction product by filtration;
further comprising removing liquid byproducts from the crude reaction product by filtration;
further comprising purifying the aminohalosilane reaction product by fractional distillation;
further comprising distilling the aminohalosilane reaction product; and
further comprising subliming the aminohalosilane reaction product.

NOTATION AND NOMENCLATURE

The following detailed description and claims utilize a number of abbreviations, symbols, and terms, which are generally well known in the art. While definitions are typically provided with the first instance of each acronym, for convenience, Table 1 provides a list of the abbreviations, symbols, and terms used along with their respective definitions.

TABLE 1

| | |
|---|---|
| a or an | One or more than one |
| Approximately or about | ±10% of the value stated |
| CVD | chemical vapor deposition |
| ALD | atomic layer deposition |
| sccm | standard cubic centimeters per minute |
| MP | melting point |
| TGA | thermogravimetric analysis |
| GCMS | gas chromatography mass spectrometry |
| alkyl group | saturated functional groups containing exclusively carbon and hydrogen atoms, including linear, branched, or cyclic alkyl groups |
| aryl | aromatic ring compounds where one hydrogen atom has been removed from the ring |
| Hetero | A functional group containing carbon and a second non-H element, such as S or O |
| heterocycle | cyclic compounds that contains atoms of at least two different elements as members of the ring structure |
| Me | Methyl |
| Et | Ethyl |
| Pr | Propyl, including iPr and nPr |
| iPr | iso-Propyl |
| nPr | n-propyl |
| Bu | Butyl, including iBu, sBu, and tBu |
| iBu | iso-Butyl |
| sBu | Sec-Butyl |
| tBu | Tert-Butyl |

The standard abbreviations of the elements from the periodic table of elements are used herein. It should be understood that elements may be referred to by these abbreviations (e.g., Si refers to silicon, N refers to nitrogen, O refers to oxygen, C refers to carbon, etc.).

Any and all ranges recited herein are inclusive of their endpoints (i.e., x=1 to 4 includes x=1, x=4 and x=any number in between).

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula $MR^1_x (NR^2R^3)_{(4-x)}$, where x is 2 or 3, the two or three $R^1$ groups may, but need not be identical to each other or to $R^2$ or to $R^3$. Further, it should be understood that unless specifically stated otherwise, values of R groups are independent of each other when used in different formulas.

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein.

DESCRIPTION OF PREFERRED EMBODIMENTS

Figure 1:
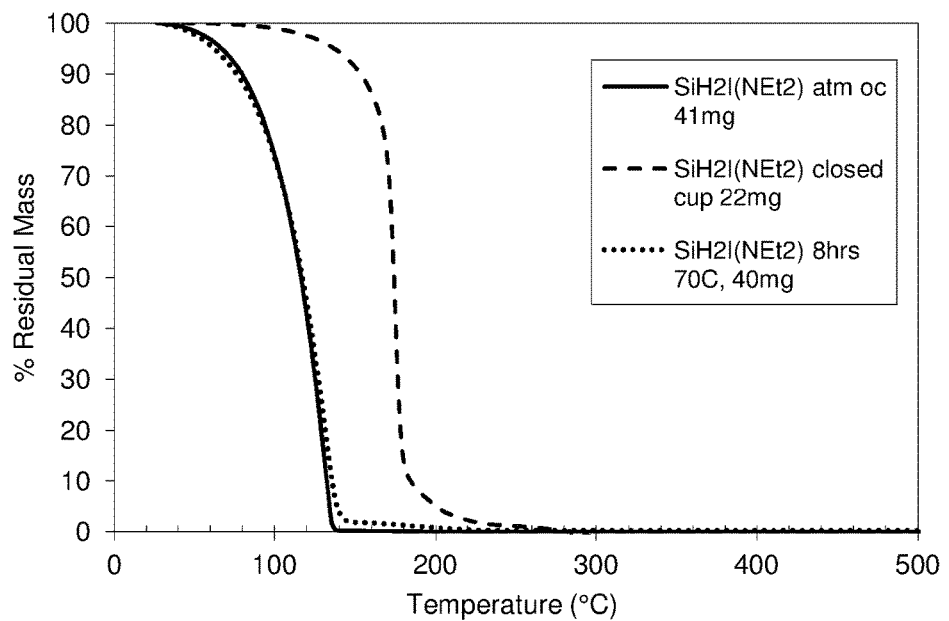
FIG. 1 is a Thermogravimetric Analysis (TGA) graph demonstrating the percentage of weight loss with increasing temperature of $SiH_2I(NEt_2)$.

Methods of synthesizing aminohalosilanes are disclosed. A halosilane having the formula

is reacted with an aminosilane having the formula

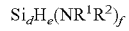

to produce the aminohalosilane reaction product having the formula:

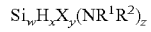

wherein X=Br or I; each R$^1$ and R$^2$ independently selected from a C$_1$-C$_{10}$ alkyl, aryl, or hetero group; a, d, and w independently=1 to 4; b+c=2a+2; b=1 to 2a+1; c=1 to 2a+1; e+f=2d+2; e=1 to 2d+1; f=1 to 2d+1; x+y+z=2w+2; x=1 to 2w; y=1 to 2w; z=1 to 2w; and R$^1$ and R$^2$ may be joined to form a nitrogen-containing heterocycle.

The disclosed methods employ a direct ligand exchange, which exchanges the X and NR$^1$R$^2$ ligands between the halosilane and aminosilane reactants. The H do not exchange.

Unlike the prior art reaction between halosilanes and amines, the disclosed methods do not produce any salt byproducts. Salt contamination and/or impurities may cause degradation of the resulting aminohalosilane reaction product. As semiconductor manufacturing requires high purity components, the ability to produce the aminohalosilane reaction products with no salt byproduct formation is beneficial.

As will be seen in the Examples that follow, the disclosed processes also produce high yields. When a=d, b=e, and the halosilane and aminosilane quantities are stoichiometrically proportional, the disclosed methods may produce one aminohalosilane reaction product, rendering obsolete the need for subsequent isolation of the reaction product from the reactants or any secondary reaction products. As a result, the disclosed methods have improved atom economy over the prior art methods because every atom in the reactant is also contained in the product. The atom economy also helps reduce waste and any further processing steps required by the prior art.

Under an inert atmosphere, the halosilane is added to a reactor at a temperature ranging from approximately −100° C. to approximately 100° C., preferably ranging from approximately −78° C. to approximately 60° C., more preferably ranging from approximately −40° C. to approximately 50° C., more preferably from approximately −25° C. to approximately 35° C., and even more preferably at approximately 0-25° C. The inert atmosphere utilized may include Ar, N$_2$, He, or Kr.

The aminosilane is then added to the flask to produce a mixture of the halosilane and aminosilane at a temperature ranging from approximately −100° C. to approximately 100° C. The aminosilane may be pre-chilled or pre-heated to the temperature equal to the temperature of the halosilane in the flask.

Alternatively, the aminosilane may be first added to the reactor under an inert atmosphere, followed by the halosilane.

The molar ratio of halosilane to aminosilane may range from approximately 10:1 to approximately 1:10 as needed to optimize the formation of the desired product and/or to simplify the purification of the desired product.

The reaction may be performed solvent free or may employ a solvent which may include but is not limited to: pentane, hexane, heptane, diethyl ether, dibutyl ether, toluene, tetrahydrofuran (THF), 2-methyltetrahydrofuran, diglyme, dichloromethane, chloroform, anisole, benzene, or acetonitrile. When one or both of the reactants and the aminohalosilane reaction product are all liquids or low melting point solids (i.e. 23-50° C.), the process is preferably performed without a solvent, which shortens the synthesis process and may also reduce the concentration of impurities in the reaction product.

The mixture is subsequently allowed to warm to room temperature and may be stirred for approximately 1 hour to approximately 48 hours at room temperature. The stirred mixture is a cloudy liquid comprising aminohalosilane, unreacted halosilane, and possible impurities.

When the aminohalosilane reaction product is a solid, the stirred mixture may be filtered to remove impurities and obtain the aminohalosilane reaction product. The product may be extracted using a solvent, such as pentane. Typical filters include glass or polymer fritted filters. The aminohalosilane reaction product may then be isolated using sublimation at a temperature range above room temperature, preferably at a range from 25° C. to 150° C., more preferably at a range from 30° C. to 120° C., even more preferably at a range from 50° C. to 70° C. Alternatively, the aminohalosilane reaction product may be isolated using sublimation at reduced pressure, preferably at a range from approximately 30 mTorr to approximately 750 Torr. In another alternative, sublimation may occur under both elevated temperature and reduced pressure.

Alternatively, when the aminohalosilane reaction product is a liquid, the stirred mixture may be filtered to remove solid byproducts. A filtration agent such as anhydrous diatomaceous earth may be employed to improve the process. Typical filters include glass or polymer frit filters. This step may be sufficient to produce the reaction product.

Occasionally, the filtrate may need further processing. For example, when the filtrate yields a heterogeneous suspension of solid material, the filtrate may then be distilled over a short path column to yield the aminohalosilane reaction product through a flash distillation process that removes some or all of the non-desired reaction products or impurities. Alternatively, the aminohalosilane reaction product may be isolated from the filtrate through a distillation column or by heating the filtrate to approximately the boiling point of the aminohalosilane. In another alternative, both the flash process and the distillation column may be necessary. One of ordinary skill in the art will recognize that the boiling point of the warmed stirred mixture will change as the aminohalosilane reaction product is isolated from the warmed stirred mixture and adjust the recovery temperature accordingly. Any unreacted halosilane may be vented through a distillation column. One of ordinary skill in the art will recognize that the vented halosilane may be recovered for later use or disposal.

The disclosed methods may convert approximately 80% mol/mol to approximately 90% mol/mol of the halosilane to the aminohalosilane reaction product. The isolated the aminohalosilane reaction product has a purity ranging from approximately 50% mol/mol to approximately 90% mol/mol.

The aminohalosilane reaction product may be further purified by distillation or sublimation. The purified the aminohalosilane reaction product has a purity ranging from approximately 97% mol/mol to approximately 100% mol/mol, preferably from approximately 99% mol/mol to approximately 100% mol/mol. The purified aminohalosilane reaction product preferably comprises between the detection limit and 100 ppbw of each potential metal contaminant (e.g., at least Al, Ca, Cr, Cu, Fe, Mg, Ni, K, Na, Ti, Zn, etc.). Suitable distillation methods include atmospheric fractional distillation or batch fractional distillation or vacuum fractional distillation. The batch fractional distillation may be performed at low temperature and pressure, but is preferably performed at atmospheric pressure. Alternatively, the the aminohalosilane reaction product may be purified by continuous distillation over two distillation columns to separate the aminohalosilane reaction product from both low and high boiling impurities in sequential steps.

As shown in the examples below, the purified product may be analyzed by gas chromatography mass spectrometry (GCMS) which shows its purity. The structure of the product may be confirmed by $^1$H, $^{13}$C and/or $^{29}$Si NMR.

One of ordinary skill in the art will recognize the sources for the equipment components of the systems used to practice the disclosed methods. Some level of customization of the components may be required based upon the desired temperature range, pressure range, local regulations, etc. Exemplary equipment suppliers include Buchi Glas Uster AG, Shandong ChemSta Machinery Manufacturing Co. Ltd., Jiangsu Shajabang Chemical Equipment Co. Ltd, etc. Preferably the components are made of corrosion resistant materials, such as stainless steel, glass lined steel, steel with corrosion resistant liners, etc.

The halosilane has the formula $Si_aH_bX_c$, wherein a=1-4; b+c=2a+2; b=1 to 2a+1; and c=1 to 2a+1. Preferably, c=2 or 3. Exemplary halosilanes include $SiH_2Br_2$, $SiH_2I_2$, $SiHBr_3$, $SiHI_3$, $Si_2H_4I_2$, $Si_2H_4Br_2$, $Si_2H_3I_3$, and $Si_2H_3Br_3$. $SiH_2I_2$, $SiHBr_3$, $SiHI_3$ are commercially available. $SiH_2Br_2$ may be synthesized as disclosed by Sato et al. in JP62070219. The synthesis of the $Si_2H_bX_c$ is disclosed by Hassler et al. in J Organometallic Chemistry (1993) 460(2), pp. 149-153. One of ordinary skill in the art will recognize that the $Si_3H_bX_c$ and $Si_4H_bX_c$ reactants may also be produced by modification of Hassler's methods. Alternatively, the halosilane reactant may be synthesized by reacting $Si_aH_{2a+2}$ with $X_2$, $BX_3$, HX with an $AlX_3$ catalyst.

As the halosilanes may degrade with time to dihalosilanes and trihalosilanes, care should be taken to ensure that the halosilane reactant has a purity ranging from approximately 90% mol/mol to approximately 100% mol/mol. Preferably, the halosilane has a purity ranging from approximately 95% mol/mol to approximately 100% mol/mol, and more preferably from approximately 98% mol/mol to approximately 100% mol/mol. Halosilane reactants having a dihalosilane content of approximately 10% mol/mol to approximately 90% mol/mol lead to low yields of amino(halo)silane due to formation of monohalosilyl disilylamine and polysilazanes. Therefore, the dihalosilane content in any halosilane reactant may range from approximately 0% mol/mol to approximately 10% mol/mol, preferably from approximately 0% mol/mol to approximately 5% mol/mol, and more preferably from approximately 0% mol/mol to approximately 1% mol/mol.

The aminosilane has the formula $Si_dH_e(NR^1R^2)_f$, wherein each $R^1$ and $R^2$ is independently selected from a $C_1$-$C_{10}$ alkyl, aryl, or hetero group; d=1-4, e+f=2d+2; e=1 to 2d+1; and f=1 to 2d+1. Preferably, f=2 or 3. Exemplary aminosilanes include bis(diisopropylamino)silane [$SiH_2(N(iPr)_2)_2$] or bis(dibutylamino)silane [$SiH_2(NiBu_2)_2$]. These aminosilanes are commercially available or may be synthesized by (1) reacting RLi with $R^1R^2$NH to form $LiNR^1R^2$ and mixing c equivalents of $LiNR^1R^2$ with $Si_aH_bX_c$ to produce $Si_aH_b(NR^1R^2)_c$ or (2) reacting 2c equivalents of $HNR^1R^2$ with $Si_aH_bX_c$ to produce $Si_aH_b(NR^1R^2)_c$. The $Si_aH_b(NR^1R^2)_c$ is purified to remove any traces of Li, $H_2NR_2^+$ or I or Br salts, which may catalyze the decomposition of the $Si_aH_b(NR^1R^2)_c$. Preferably, the aminosilane has a purity ranging from approximately 95% mol/mol to approximately 100% mol/mol, and more preferably from approximately 98% mol/mol to approximately 100% mol/mol. The Li, $H_2NR_2^+$ or I or Br salts content may range from approximately 0% mol/mol to approximately 10% mol/mol, preferably from approximately 0% mol/mol to approximately 5% mol/mol, and more preferably from approximately 0% mol/mol to approximately 1% mol/mol.

The halosilane or aminosilane may be mixed with a solvent, particularly if either is a solid. The ratio of solvent to halosilane or aminosilane is chosen from the range of approximately 3 mL to approximately 20 mL of the solvent per approximately 1 g of the halosilane or aminosilane, preferably approximately 6 mL to approximately 8 mL of the solvent per approximately 1 g of the halosilane or aminosilane. One of ordinary skill in the art will recognize that a neat, non-solvent process may still be performed if only one of the halosilane or aminosilane is a solid.

The solvent may be selected from arenes, alkanes, alkenes, cycloalkanes or alkyne-based compounds. The selected solvent is not reactive with any of the reactants or products. Furthermore, the solvent must be a liquid at the reaction temperature. Therefore, the selected solvent remains a liquid at temperatures ranging between −100° C. and the boiling point of the solvent. Finally, the solvent must be dry in order to prevent the formation of oxygenated species, such as disiloxanes. The solvent may contain between approximately 0 ppmv and approximately 100 ppmv moisture, and preferably between approximately 0 ppmv and approximately 10 ppmv moisture.

Exemplary solvents include hexane, toluene, heptane, ethylbenzene, or one or more of the xylenes. The xylenes are 1,2-dimethylbenzene, 1,3-dimethylbenzene, and 1-4-dimethylbenzene. Preferably, the solvents are hexane or toluene because they do not freeze at −78° C. Other solvents having properties similar to hexane and toluene are also preferable in the disclosed methods.

The following is a list of exemplary aminohalosilane reaction products produced by the disclosed synthesis methods.

When X=Br, w=1, x=2, y=1, and z=1, the exemplary reaction is $SiH_2Br_2+SiH_2(NR^1R^2)_2 \rightarrow$

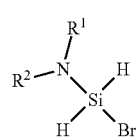

wherein $R^1$ and $R^2$ is selected from a $C_1$-$C_{10}$ alkyl, aryl, or hetero group. When stoichiometric quantities of the reactants are used, the process produces one reaction product.

Exemplary aminohalosilanes having the formula $SiH_2Br(NR^1R^2)$ include:

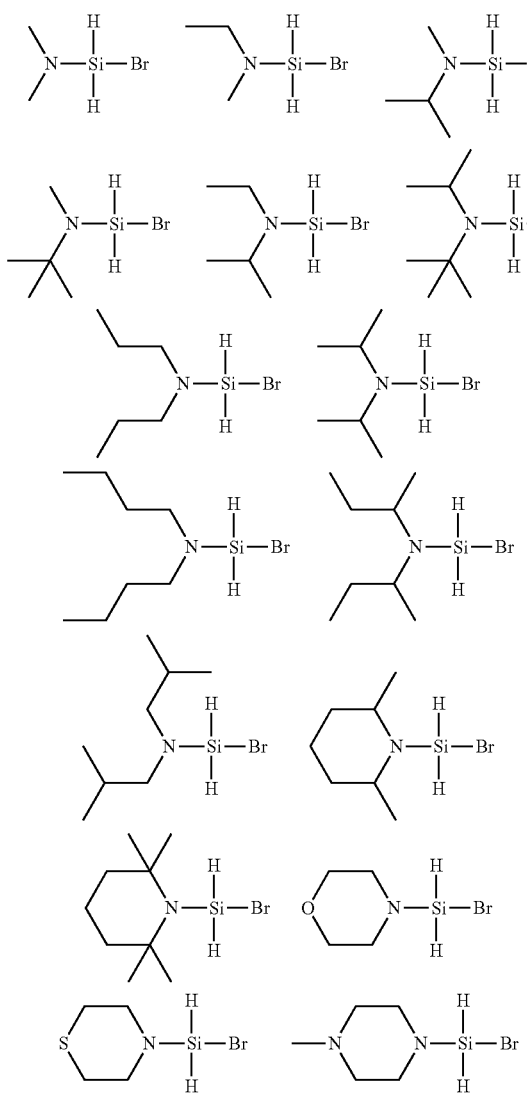

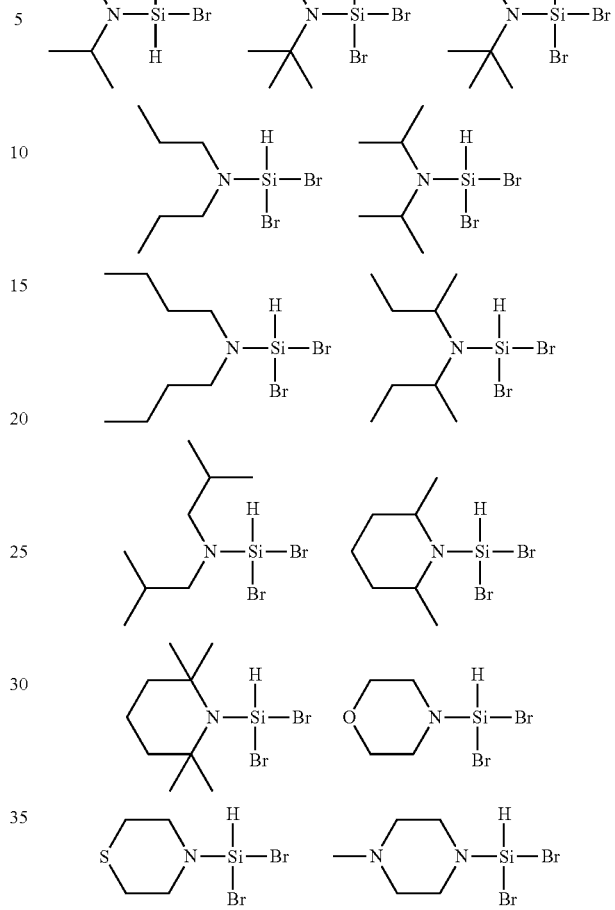

When X=Br, w=1, x=1, y=2, and z=1, the exemplary reaction is 2 SiHBr$_3$+SiH(NR$^1$R$^2$)$_3$→

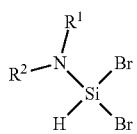

wherein R$^1$ and R$^2$ is selected from a C$_1$-C$_{10}$ alkyl, aryl, or hetero groups. When stoichiometric quantities of the reactants are used, the process produces one reaction product.

Exemplary aminohalosilanes having the formula SiHBr$_2$(NR$^1$R$^2$) include:

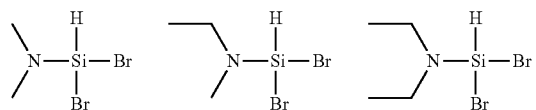

When X=Br, w=1, x=1, y=1, and z=2, the exemplary reaction is SiHBr$_3$+2 SiH(NR$^1$R$^2$)$_3$→

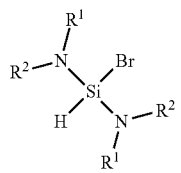

wherein each R$^1$ and R$^2$ is independently selected from a C$_1$-C$_{10}$ alkyl, aryl, or hetero group. When stoichiometric quantities of the reactants are used, the process produces one reaction product.

Exemplary aminohalosilanes having the formula SiHBr(NR$^1$R$^2$)$_2$ include:

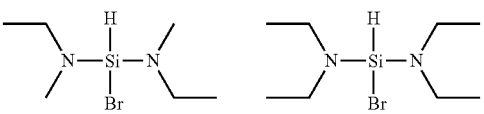

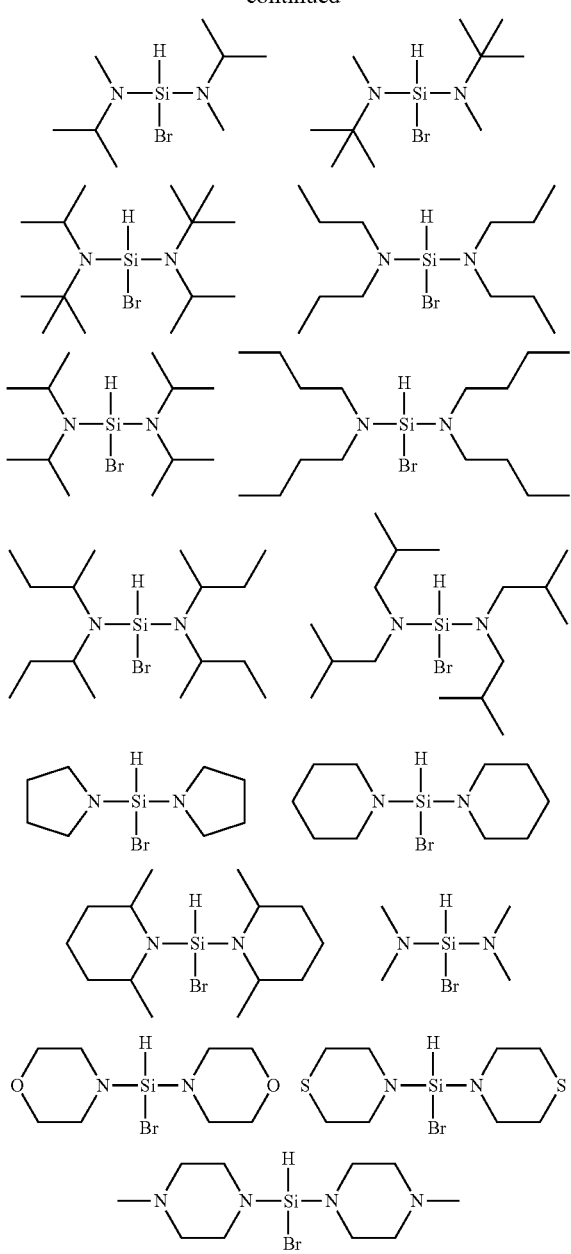

When X=Br, w=1, x=0, y=3, and z=1, the exemplary reaction is 3 SiBr$_4$+Si(NR$^1$R$^2$)$_4\rightarrow$

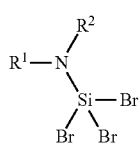

wherein R$^1$ and R$^2$ is selected from a C$_1$-C$_{10}$ alkyl, aryl, or hetero group. When stoichiometric quantities of the reactants are used, the process produces one reaction product.

Exemplary aminohalosilanes having the formula SiBr$_3$(NR$^1$R$^2$) include:

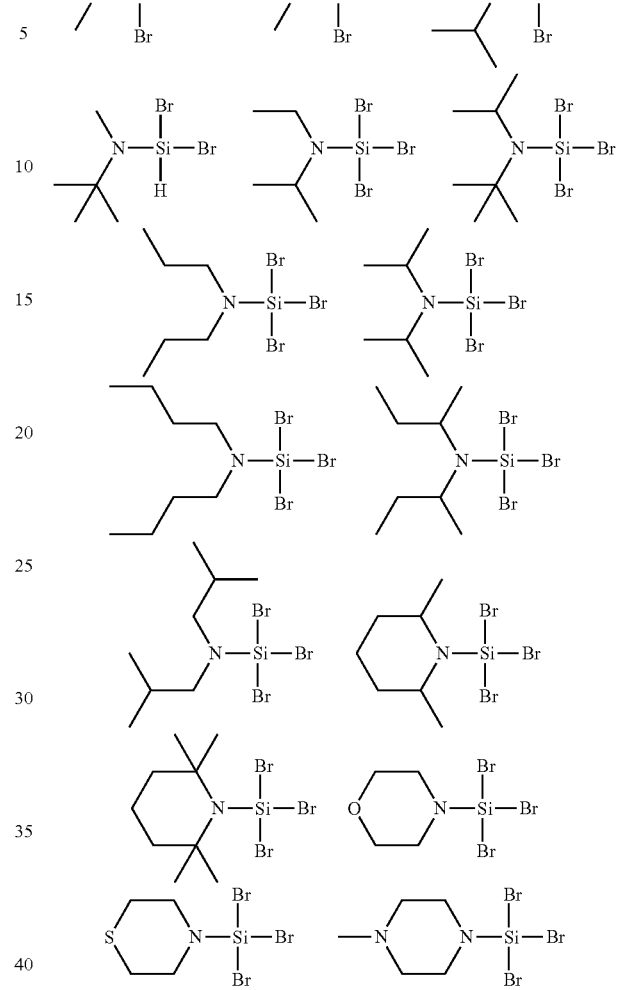

When X=Br, w=1, x=0, y=2, and z=2, the exemplary reaction is SiBr$_4$+Si(NR$^1$R$^2$)$_4\rightarrow$

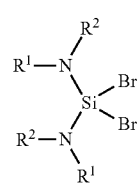

wherein each R$^1$ and R$^2$ is independently selected from a C$_1$-C$_{10}$ alkyl, aryl, or hetero group. When stoichiometric quantities of the reactants are used, the process produces one reaction product.

Exemplary aminohalosilanes having the formula SiBr$_2$(NR$^1$R$^2$)$_2$ include:

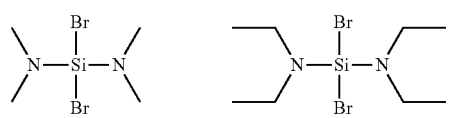

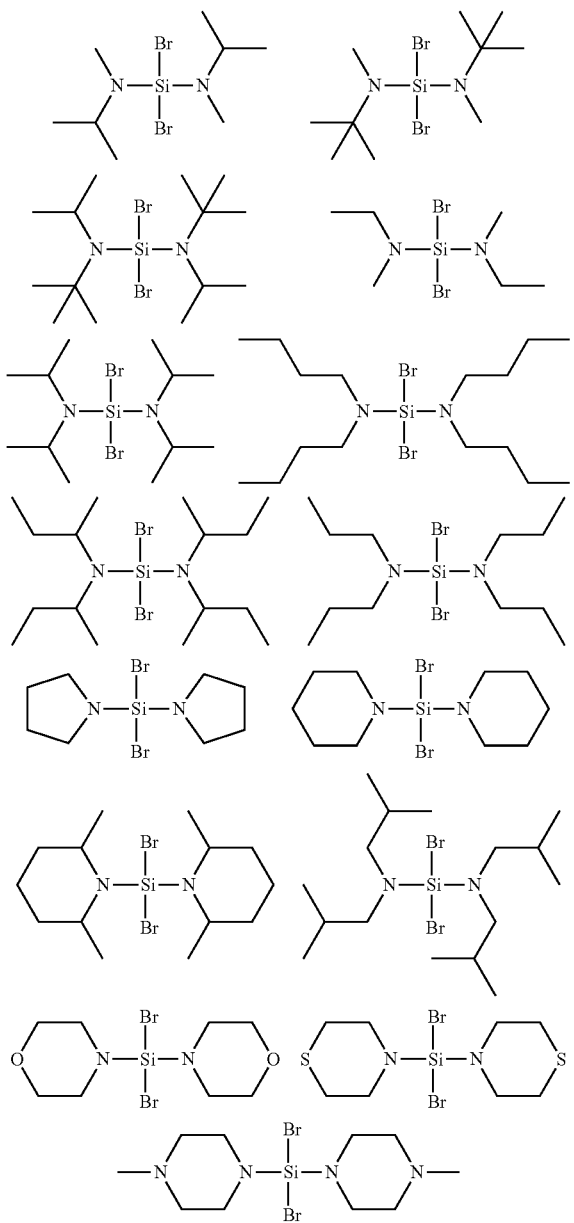

When X=Br, w=1, x=0, y=1, and z=3, the exemplary reaction is $SiH_2Br_2 + Si(NR^1R^2)_4 \rightarrow$

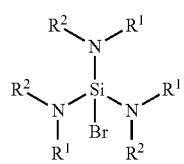

wherein each $R^1$ and $R^2$ is independently selected from a $C_1$-$C_{10}$ alkyl, aryl, or hetero group. One of ordinary skill in the art will recognize that $SiH_2Br(NR^1R^2)$ will also be formed.

Exemplary aminohalosilanes having the formula $SiBr(NR^1R^2)_3$ include:

When X=I, w=1, x=2, y=1, and z=1, the exemplary reaction is $SiH_2I_2 + SiH_2(NR^1R^2)_2 \rightarrow$

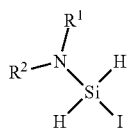

wherein $R^1$ and $R^2$ is selected from $C_1$-$C_{10}$ alkyl, aryl, or hetero group. When stoichiometric quantities of the reactants are used, the process produces one reaction product.

Exemplary aminohalosilanes having the formula $SiH_2I$ $(NR^1R^2)$ include:

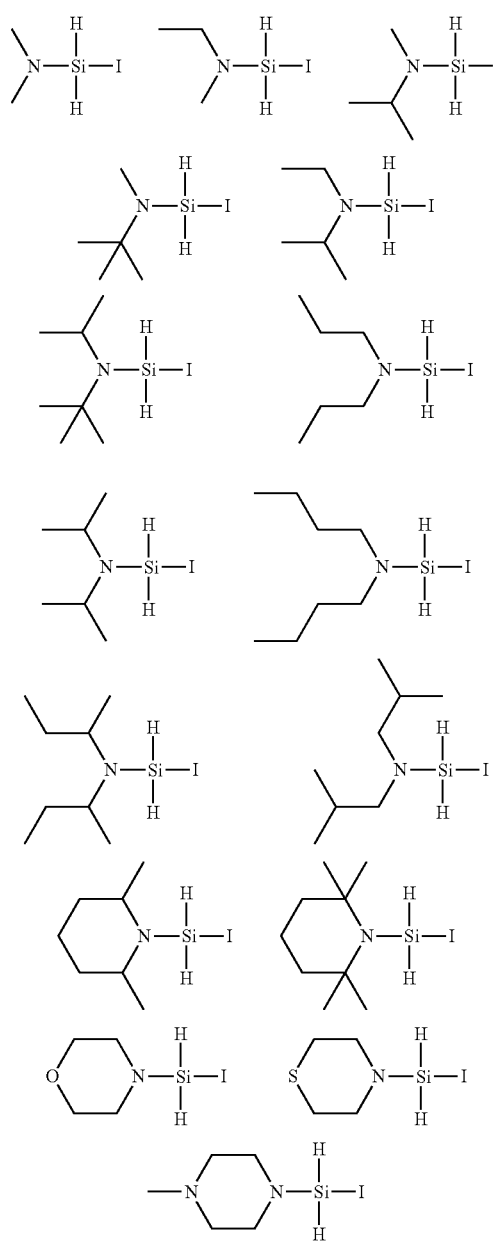

When X=I, w=1, x=1, y=2, and z=1, the exemplary reaction is $2\ SiHI_3 + SiH(NR^1R^2)_3 \rightarrow$

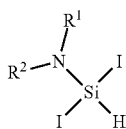

wherein $R^1$ and $R^2$ is selected from a $C_1$-$C_{10}$ alkyl, aryl, or hetero group. When stoichiometric quantities of the reactants are used, the process produces one reaction product.

Exemplary aminohalosilanes having the formula $SiHI_2$ $(NR^1R^2)$ include:

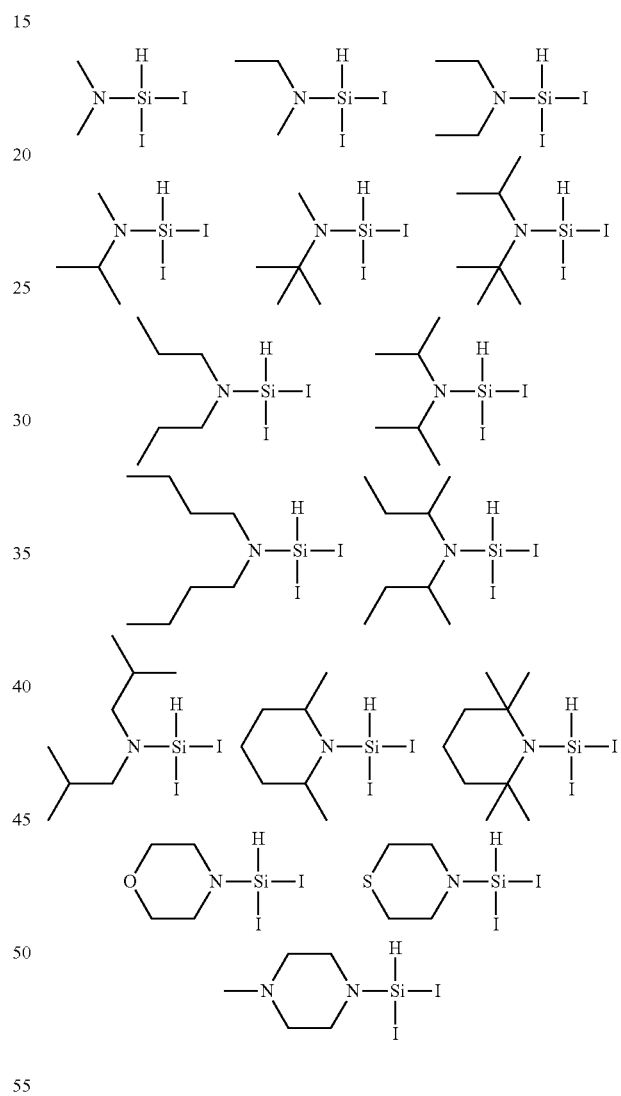

When X=I, w=1, x=1, y=1, and z=2, the exemplary reaction is $SiHI_3 + 2\ SiH(NR^1R^2)_3 \rightarrow$

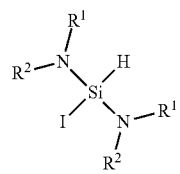

wherein each $R^1$ and $R^2$ is independently selected from a $C_1$-$C_{10}$ alkyl, aryl, or hetero group. When stoichiometric quantities of the reactants are used, the process produces one reaction product Exemplary aminohalosilanes having the formula SiHI$(NR^1R^2)_2$ include:

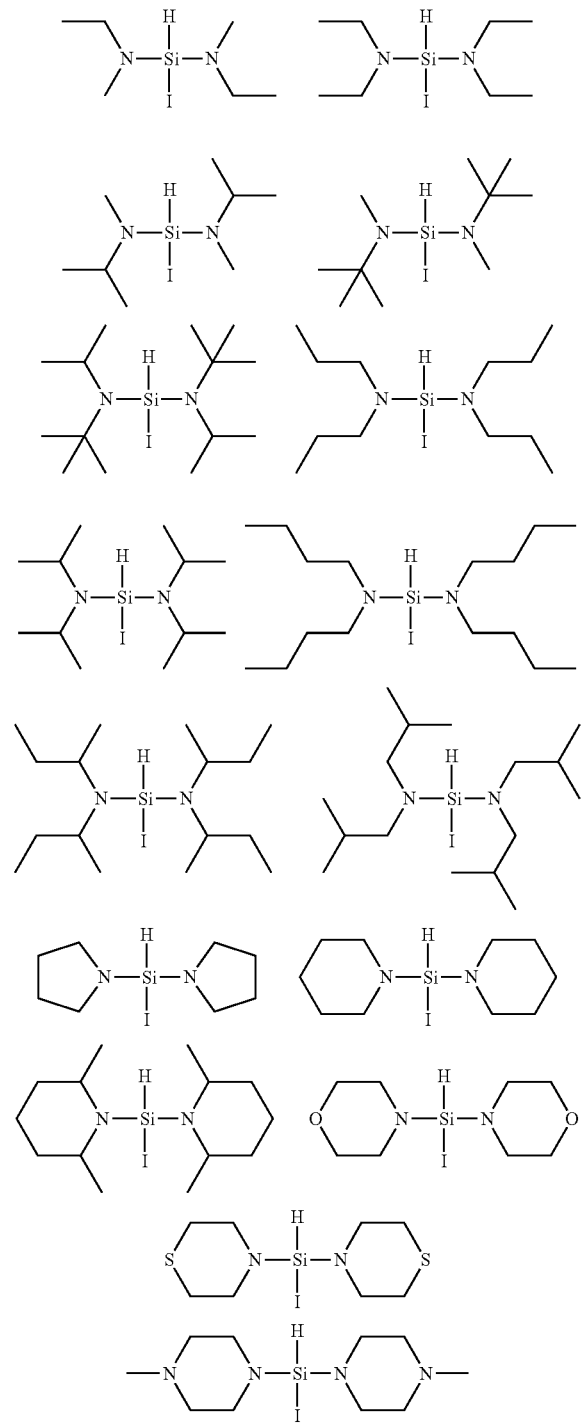

When X=I, w=1, x=0, y=3, and z=1, the exemplary reaction is 3 SiI$_4$+Si$(NR^1R^2)_4$→

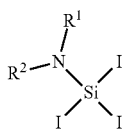

wherein $R^1$ and $R^2$ is selected from a $C_1$-$C_{10}$ alkyl, aryl, or hetero group. Preferably, as shown in Comparative Example 1, at least one of $R^1$ or $R^2$ is $C_2$-$C_{10}$. When stoichiometric quantities of the reactants are used, the process produces one reaction product.

Exemplary aminohalosilanes having the formula SiI$_3$$(NR^1R^2)$ include:

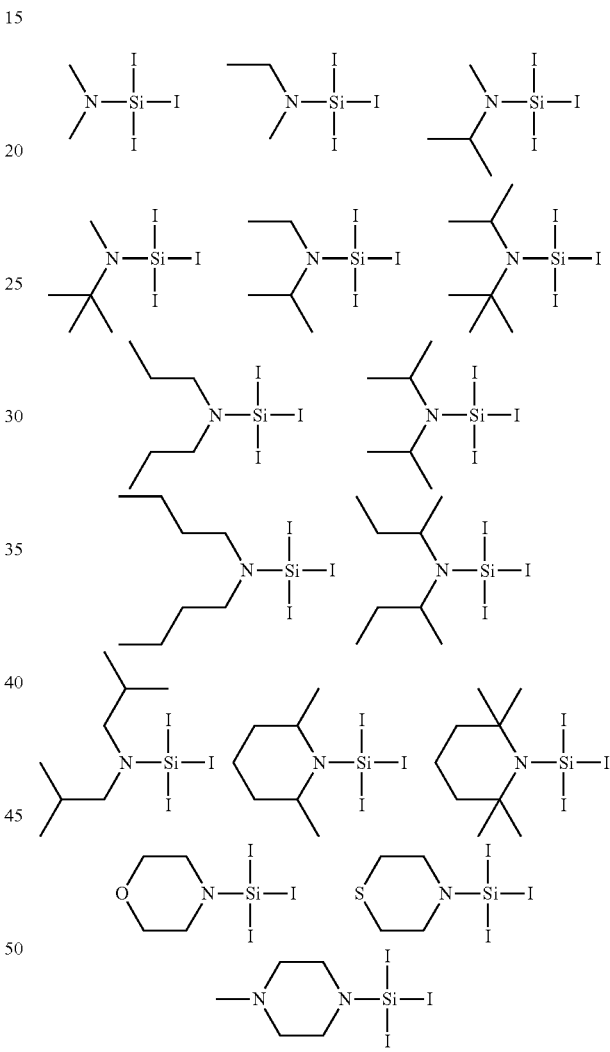

When X=I, w=1, x=0, y=2, and z=2, the exemplary reaction is SiI$_4$+Si$(NR^1R^2)_4$→

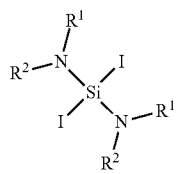

wherein each $R^1$ and $R^2$ is independently selected from a $C_1$-$C_{10}$ alkyl, aryl, or hetero group. When stoichiometric quantities of the reactants are used, the process produces one reaction product.

Exemplary aminohalosilanes having the formula $SiI_2(NR^1R^2)_2$ include:

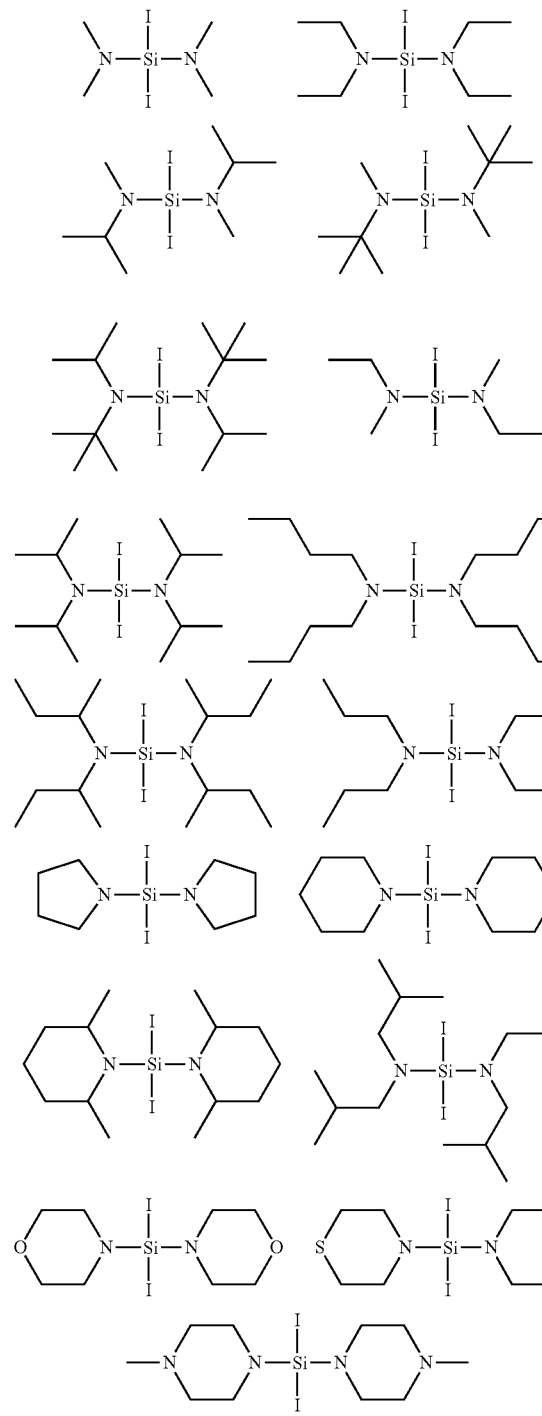

When X=I, w=1, x=0, y=1, and z=3, the exemplary reaction is $SiH_2I_2+Si(NR^1R^2)_4\rightarrow$

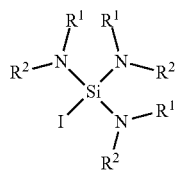

wherein each $R^1$ and $R^2$ is independently selected from a $C_1$-$C_{10}$ alkyl, aryl, or hetero group. One of ordinary skill in the art will recognize that $SiH_2Br(NR^1R^2)$ will also be formed.

Exemplary aminohalosilanes having the formula $SiI(NR^1R^2)_3$ include:

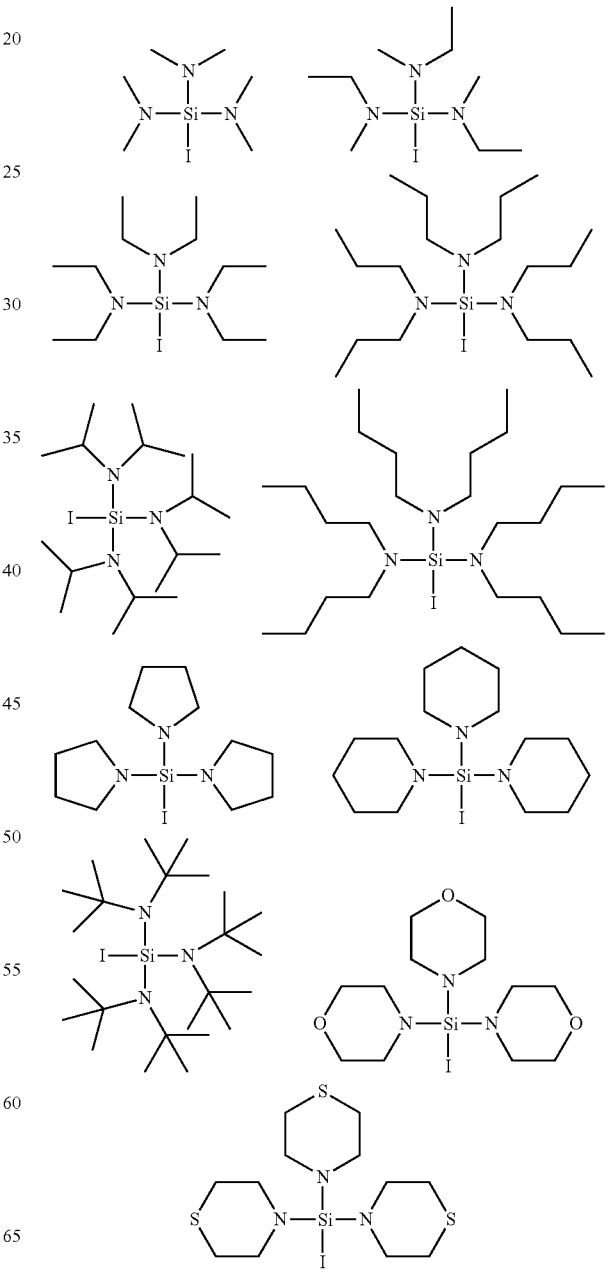

-continued

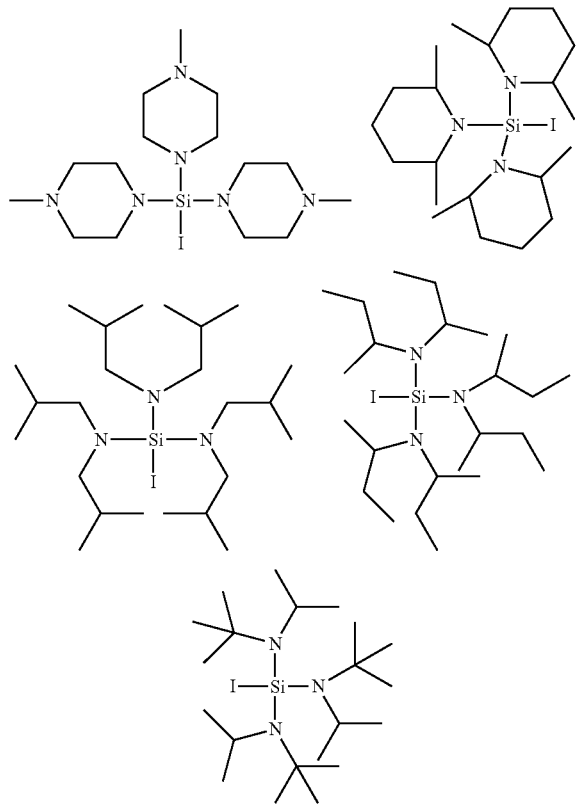

When X=I, w=2, x=4, y=1, and z=1, the exemplary reaction is $Si_2H_4I_2+Si_2H_4(NR^1R^2)_2 \rightarrow$

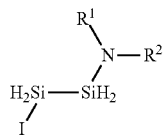

wherein each $R^1$ and $R^2$ is independently selected from a $C_1$-$C_{10}$ alkyl, aryl, or hetero group. When stoichiometric quantities of the reactants are used, the process produces one reaction product. Alternatively, as shown in the examples that follow, the halosilane may be $SiH_2I_2$, but multiple reaction products are formed.

Exemplary aminohalodisilanes having the formula $Si_2H_4I(NR^1R^2)$ include:

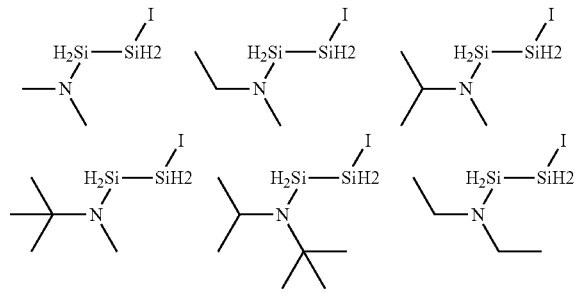

-continued

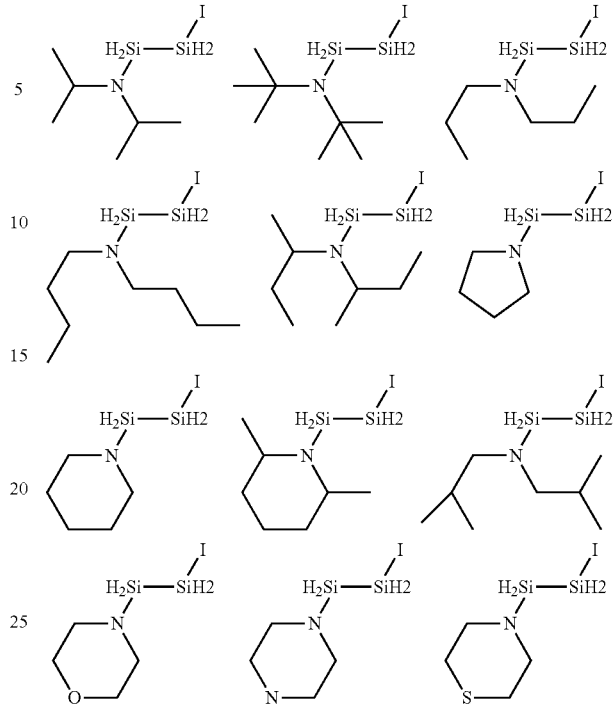

When X=Br, w=2, x=4, y=1, and z=1, the exemplary reaction is $Si_2H_4Br_2+Si_2H_4(NR^1R^2)_2 \rightarrow$

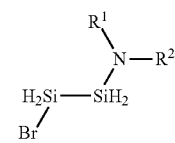

wherein each $R^1$ and $R^2$ is independently selected from a $C_1$-$C_{10}$ alkyl, aryl, or hetero group. When stoichiometric quantities of the reactants are used, the process produces one reaction product.

Exemplary aminohalodisilanes having the formula $Si_2H_4Br(NR^1R^2)$ include:

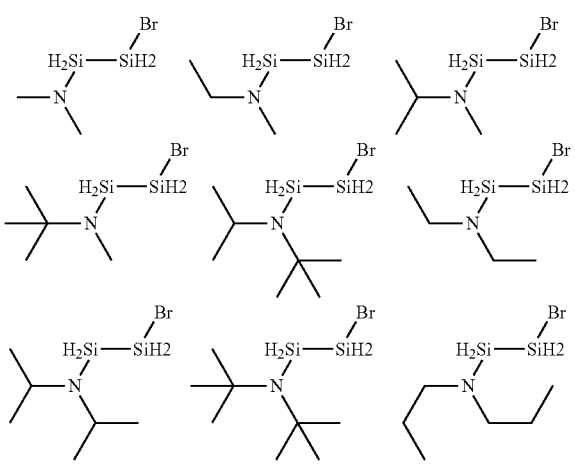

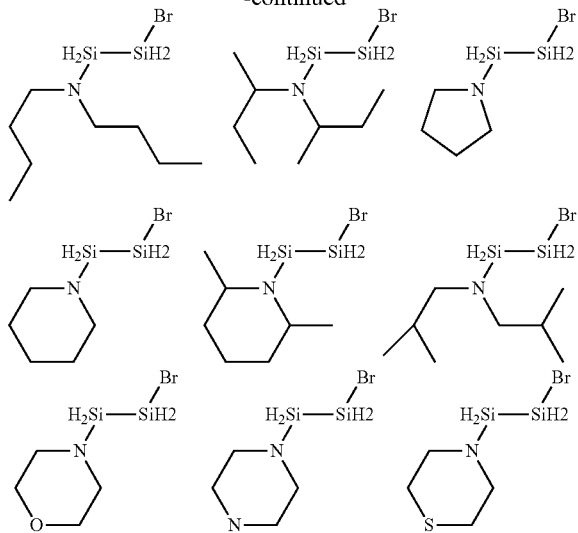

Exemplary aminohalosilane reaction products may be selected from SiH$_2$Br(N(Et)$_2$), SiH$_2$Br(N(iPr)$_2$), SiH$_2$Br(N(iBu)$_2$), SiBr(NMe$_2$)$_3$, SiH$_2$I(N(Et)$_2$), SiH$_2$I(N(iPr)$_2$), SiH$_2$I(N(iBu)$_2$) or SiI(NMe$_2$)$_3$.

EXAMPLES

The following non-limiting examples are provided to further illustrate embodiments of the invention. However, the examples are not intended to be all inclusive and are not intended to limit the scope of the inventions described herein.

Example 1

Synthesis of diethylamino(iodo)silane SiH$_2$I(NEt$_2$)

Synthesis Route: SiH$_2$(NEt$_2$)$_2$+SiH$_2$I$_2$→2SiH$_2$I(NEt$_2$) (Neat Reaction).

Under an atmosphere of pure N$_2$, a flask is charged with diiodosilane (SiH$_2$I$_2$) (41.2 g, 0.145 mol) and cooled to 0° C. Bis(diethylamino)silane (SiH$_2$(NEt$_2$)$_2$) (25.4 g, 0.146 mol) is chilled to 0° C. and then added at a rate of ~0.5 mL/minute to the reaction flask. Fuming is observed during the course of the addition. The reaction is subsequently allowed to warm to room temperature and stirred for 4 hours to obtain a cloudy, pale yellow liquid.

The crude product is then distilled over a short path column (30-32° C., 1.2 mTorr) to yield a colorless, air sensitive, free flowing liquid (57.3 g, 85% yield). The product was analyzed by GCMS which shows >99% purity. The structure of the product is confirmed by $^1$H, $^{13}$C & $^{29}$Si NMR.

Distilled SiH$_2$I(NEt$_2$) TGA is shown in FIG. 1. Open cup TGA shows clean evaporation and low (<1%) residue for SiH$_2$I(NEt$_2$) both before and after heating to 70° C. for 8 hours but thermally stressed material shows a small step behavior (due to small % of decomposition). The closed cup measurement shows step behavior over ~180° C. Thermal stability tests of SiH$_2$I(NEt$_2$) show solids formation upon heating over time.

The properties of SiH$_2$I(NEt$_2$) are as follows.
Distilled SiH$_2$I(NEt$_2$) Vapor pressure=10 Torr @ 27° C.
Isolated Yield=57.3 g (86% unoptimized).
MP=<−70° C.
TGA residue (oc)=<1%.
Thermal Test (8 hrs @ 80° C.) shows <1% decomposition.
Purity (GCMS & $^1$H NMR) >99%.

Example 2

Synthesis of diisopropylamino(iodo)silane SiH$_2$I(NiPr$_2$)

Synthesis Route: SiH$_2$I$_2$+SiH$_2$(NiPr$_2$)$_2$→2SiH$_2$I(NiPr$_2$) (Neat Reaction)

Under an atmosphere of pure N$_2$, a flask is charged with diiodosilane (28.5 g, 0.100 mol). At 24° C., bis(diisopropylamino)silane (23.4 g, 0.101 mol) is added at a rate of ~1 mL/minute and stirred for 4 hours to obtain a cloudy, pale yellow liquid.

The crude product is then distilled over a short path column (25-30° C., 80-120 mTorr) to yield a colorless, air sensitive, free flowing liquid (43.2 g, 84% yield). The product was analyzed by GCMS which shows >99% purity. Structure confirmed by $^1$H, $^{13}$C & $^{29}$Si NMR.

Figure 2:
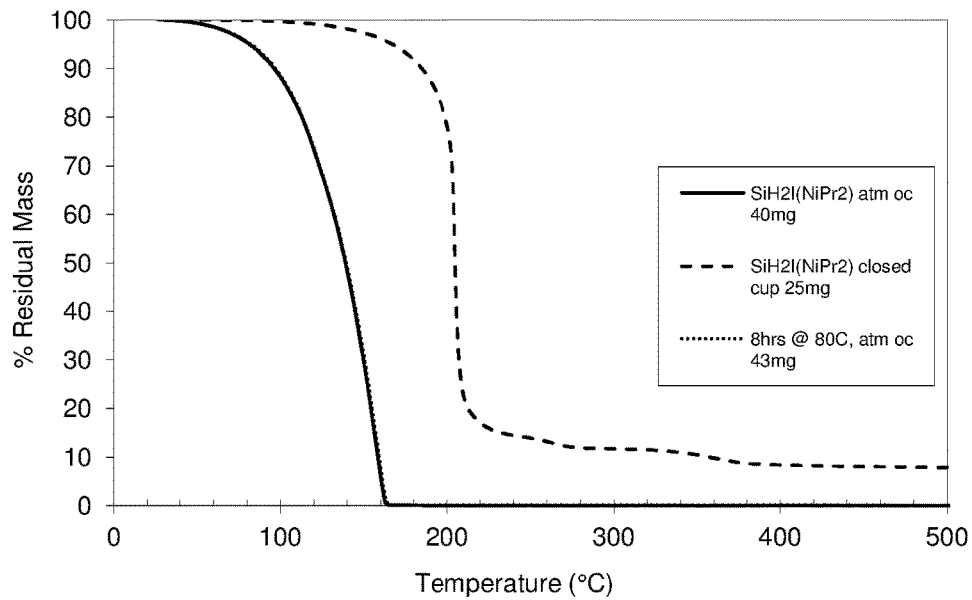
FIG. 2 is a TGA graph demonstrating the percentage of weight loss with increasing temperature of $SiH_2I(N^iPr_2)$.

Distilled SiH$_2$I(N(iPr)$_2$) TGA is shown in FIG. 2. The open cup TGA shows clean evaporation and low (<1%) residue for SiH$_2$I(N(iPr)$_2$) both before and after heating to 80° C. for 8 hours: demonstrating the good stability of this product. The closed cup measurement shows step behavior over 200° C. Thermal Test @ 80° C. for 8 hrs demonstrates <1% decomposition showing solids formation upon heating over time.

The properties of SiH$_2$I(N(iPr)$_2$) are as follows.
Distilled SiH$_2$I(N(iPr)$_2$) Vapor pressure @ 41° C. is 10 Torr.
Isolated Yield is 43.2 g (84%).
MP is −8° C.
Appearance: colorless liquid.
Purity (GCMS & $^1$H NMR) shows >99% purity product SiH$_2$I(N(iPr)$_2$).
$^1$H & $^{29}$Si NMR confirms GCMS, shows single product SiH$_2$I(N(iPr)$_2$).
$^{13}$C NMR shows expected peaks for clean product SiH$_2$I(N(iPr)$_2$).
Density @ 24° C. is 1.35 g/mL.
Viscosity @ 24° C. is 1.42 cSt.

Example 3

Synthesis of dibutylamino(iodo)silane SiH$_2$I(N(iBu)$_2$)

Synthesis Route: SiH$_2$I$_2$+SiH$_2$(N(iBu)$_2$)$_2$→2SiH$_2$I(N(iBu)$_2$) (Neat Reaction)

Under an atmosphere of pure N$_2$, a flask is charged with diiodosilane (15.6 g, 0.055 mol) and cooled to 0° C. Bis(dibutylamino)silane (15.8 g, 0.055 mol) is chilled to 0° C. and then added at a rate of ~1 mL/minute to the reaction flask. Fuming is observed initially. The reaction is subsequently allowed to warm to room temperature and stirred for 6 hours to obtain a cloudy, pale yellow liquid.

The crude product is then distilled over a short path column (33-37° C., 50-70 mTorr) to yield a colorless, air sensitive, free flowing liquid (27.6 g, 88% yield). The product was analyzed by GCMS which shows >99% purity. Structure confirmed by $^1$H, $^{13}$C & $^{29}$Si NMR.

Figure 3:
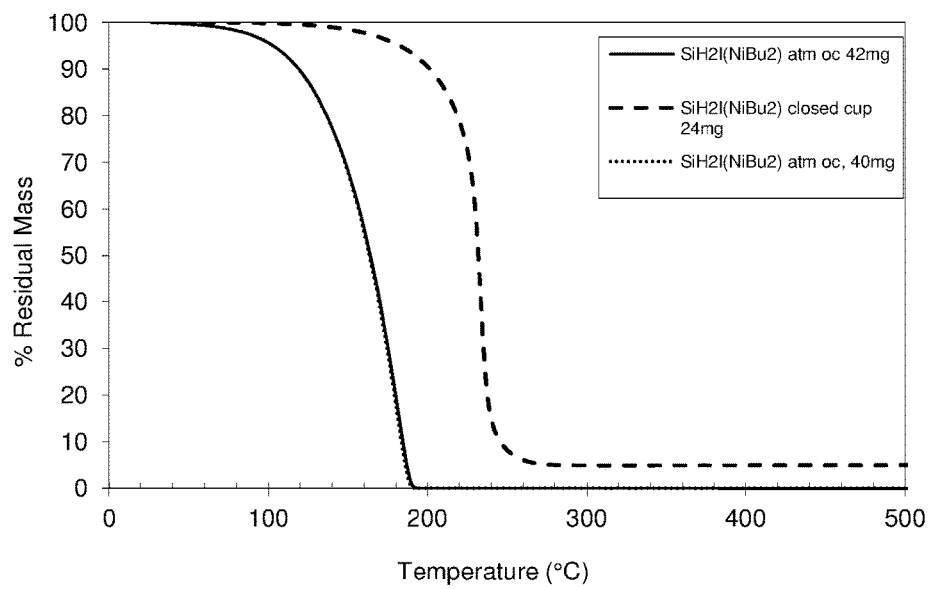
FIG. 3 is a TGA graph demonstrating the percentage of weight loss with increasing temperature of $SiH_2I(N^iBu_2)$.

Distilled SiH$_2$I(N(iBu)$_2$) TGA is shown in FIG. 3. The open cup TGA shows clean evaporation and low (<1%)

residue for SiH$_2$I(N(iBu)$_2$) both before and after 8 hour thermal test @ 70° C. The closed cup TGA shows slightly higher residue (~4%).

The properties of SiH$_2$I(N(iBu)$_2$) are as follows.
Distilled SiH$_2$I(N(iBu)$_2$) Vapor Pressure=1 Torr @ 29° C.
Isolated Yield=27.6 g (~88%) [distillation conditions: 33-37° C. @ 50-70 mTorr].
MP=<−70° C.
TGA residue (oc) <1%.
Appearance is colorless liquid.
Thermal Test (8 hrs @ 80° C.) <1% decomposition.
$^1$H & $^{29}$Si NMR confirms GCMS shows single product SiH$_2$I(N(iBu)$_2$).
$^{13}$C NMR confirms GCMS shows single product SiH$_2$I(N(iBu)$_2$).
Purity (GCMS & $^1$H NMR) >99%.
Density=1.28 g/mL @ 24° C.
Viscosity=1.79 cSt @ 24° C.

Example 4

Synthesis of bis(dimethylamino)iodosilane
SiHI(NMe$_2$)$_2$

Synthesis Route: SiHI$_3$+SiH(NMe$_2$)$_3$→2SiHI(NMe$_2$)$_2$ (Neat Reaction)

A flask containing tris(dimethylamino)silane (15.9 g, 0.099 mol) under an atmosphere of dry N$_2$ is chilled to 0° C. and triiodosilane (20.4 g, 0.049 mol) is added at a rate of ~1 mL/minute. Some fuming is observed initially. The reaction is subsequently allowed to warm to room temperature and stirred for 16 hours to obtain a slightly cloudy, pale yellow liquid. The product is distilled over a short path column (30-35° C., 80-110 mTorr) to yield a colorless, air sensitive, free flowing liquid (23.3 g, 65% yield). The product identified as bis(dimethylamino)iodosilane was analyzed by GCMS which shows >95% purity. Structure and purity were confirmed by $^1$H & $^{13}$C NMR.

Figure 4:
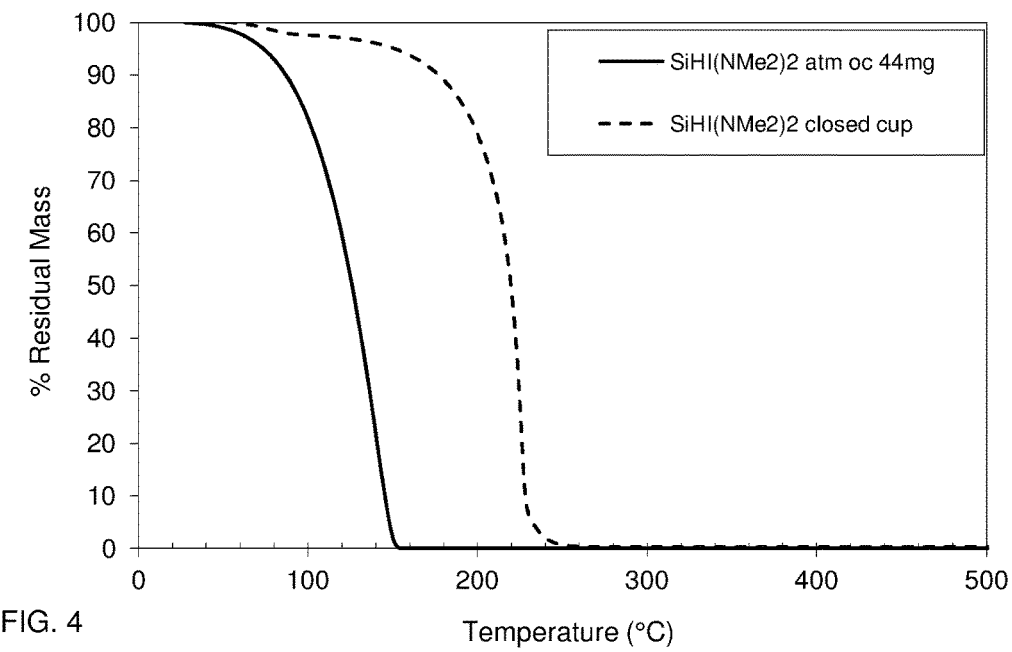
FIG. 4 is a TGA graph demonstrating the percentage of weight loss with increasing temperature of $SiHI(NMe_2)_2$.

The TGA analysis of SiHI(NMe$_2$)$_2$ is shown in FIG. 4. Both the open cup and closed cup TGA graphs show clean evaporation with a low (<1%) residue. The closed cup TGA shows a slight step at 100° C. due to presence of a small amount of starting material in the product.

Example 5

Synthesis of (diisopropylamino)bromodisilane
[SiH$_2$Br(N$^i$Pr$_2$)]

Synthesis Route: SiBr$_4$+SiH$_2$(NiPr$_2$)$_2$→SiH$_2$Br(NiPr$_2$)+SiBr$_3$(NiPr$_2$) (in CHCl$_3$)

A flask equipped with a reflux condenser and containing a chloroform (100 mL) solution of bis(diisopropylamino)silane (27.4 g, 0.119 mol) under an atmosphere of dry N$_2$ is chilled to 0° C. and tetrabromosilane (41.8 g, 0.120 mol) is added at a rate of ~1 mL/minute. The reaction is subsequently allowed to warm to room temperature and then heated with stirring for 9 hours to obtain a cloudy, colorless suspension. A sample of the reaction mixture is dissolved completely into dichloromethane (1 mL) and analyzed by GCMS which shows greater than 99% conversion to the products (diisopropylamino)bromosilane and (diisopropylamino)tribromosilane with less than 1% remaining of the starting reagent tetrabromosilane and less than 0.1% remaining of bis(diisopropylamino)silane.

Example 6

Synthesis of mono(diisopropylamino)iododisilane
[H$_2$ISi—SiH$_2$(N$^i$Pr$_2$)]

Synthesis Route: SiH$_2$I$_2$+(NiPr$_2$)H$_2$Si—SiH$_2$(NiPr$_2$)→SiH$_2$I(NiPr$_2$)+H$_2$ISi—SiH$_2$(N$^i$Pr$_2$)(in C$_5$H$_{12}$)

Under an atmosphere of dry N$_2$, anhydrous pentane (20.0 mL, 0.174 mol) was added to a flask containing diiodosilane (2.1 g, 7.34 mmol) and equipped with a condenser. 1,2-bis(diisopropylamino)disilane (1.9 g, 7.34 mmol) is added and the mixture heated with stirring to form a yellow solution at room temperature for 2 hours. An aliquot was taken for analysis by GCMS. The composition of the silicon containing products is observed as follows: SiI(N$^i$Pr$_2$)H$_2$ (70.3%), H$_2$ISi—SiH$_2$(N$^i$Pr$_2$), (29.7%).

Figure 5:
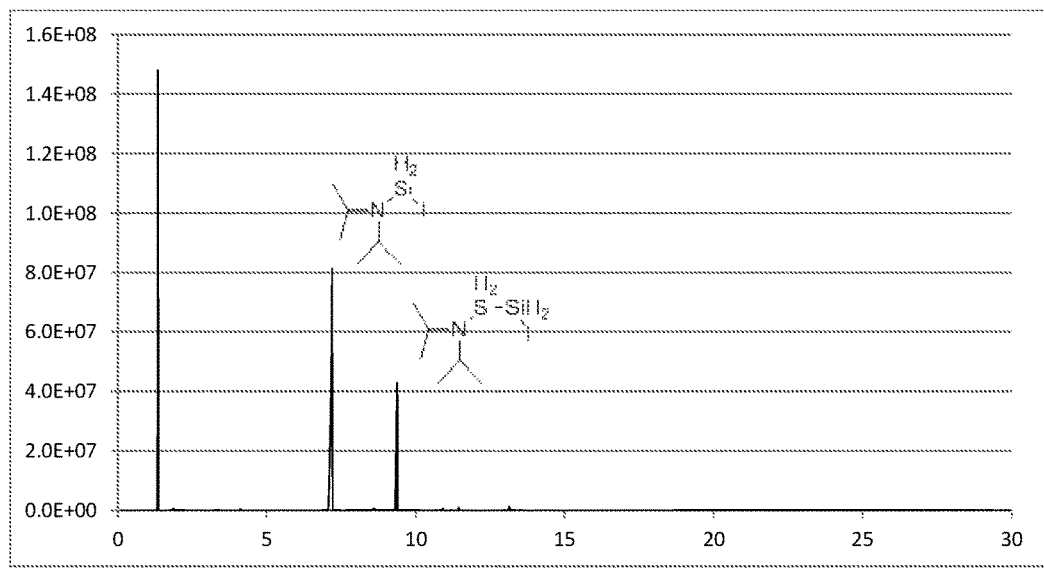
FIG. 5 is the GC chromatogram of the sample of the reaction mixture produced in Example 6.
Figure 6:
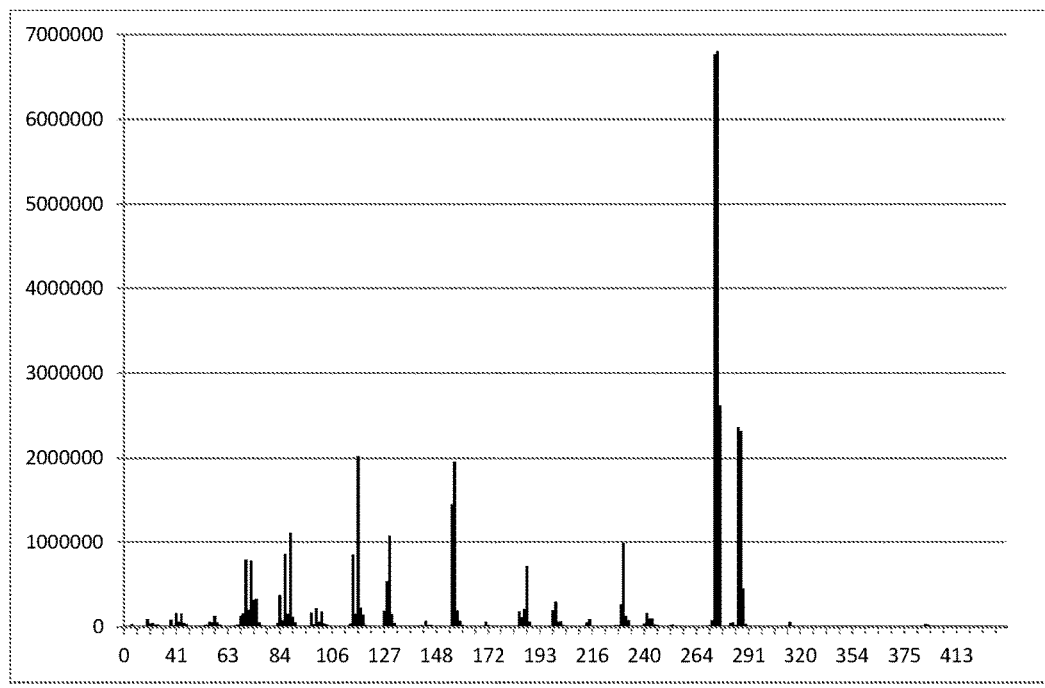
FIG. 6 is a graph of the mass spectrum of the compound H$_2$ISi—SiH$_2$(N$^i$Pr$_2$) produced in Example 6.

FIG. 5 is the GC chromatogram of the sample of the mixture taken after reaction. FIG. 6 shows the mass spectrum of the compound H$_2$ISi—SiH$_2$(N$^i$Pr$_2$).

Comparative Example 1

Synthesis of bis(dimethylamino)diiodosilane
[SiI$_2$(NMe$_2$)$_2$]

Synthesis Route: SiI$_4$+Si(NMe$_2$)$_4$→Si(NMe$_2$)$_4$, SiI(NMe$_2$)$_3$, SiI$_2$(NMe$_2$)$_2$, SiI$_3$(NMe$_2$) and SiI$_4$ (in Toluene)

Under an atmosphere of dry N$_2$, anhydrous toluene (30.0 mL, 0.284 mol) was added to a flask containing silicon tetraiodide (25.2 g, 0.047 mol) and equipped with a condenser. Tetrakis(dimethylamino)silane (10.4 g, 0.051 mol) is added followed by triethylamine (1.0 mL, 0.007 mol) and the mixture heated with stirring to form a yellow solution at 90° C. for 6 hours. The reaction is cooled to 23° C. and an aliquot taken for analysis by GCMS. The composition of the silicon containing products is observed as follows: Si(NMe$_2$)$_4$ (60.1%), SiI(NMe$_2$)$_3$, (2.2%), SiI$_2$(NMe$_2$)$_2$ (3.1%), SiI$_3$(NMe$_2$) (3.7%) and SiI$_4$ (30.9%). In other words, the reaction between SiI$_4$ and Si(NR$_2$)$_4$ is not as "fruitful" as the reaction between SiCl$_4$ and Si(NR$_2$)$_4$ reported by Passarelli et al., demonstrating that the halides do not always behave similarly. Dalt. Trans., 2003, at 417.

Comparative Example 2

Synthesis of (tert-butylamino)iodosilane [SiH$_2$I(NH$^t$Bu)]

Synthesis Route: SiH$_2$I$_2$+SiH$_2$(NHtBu)$_2$  SiH$_2$I(NHtBu) (Neat)

Under an atmosphere of dry N$_2$ at 23° C., bis(tert-butylamino)silane (1.72 g, 9.86 mmol) is added dropwise to a flask containing diodosilane (2.80 g, 9.86 mmol). Some fuming and the formation of colorless solids are observed. A sample of the product mixture is dissolved in dichloromethane (0.5 mL, 7.83 mmol) and analyzed by GCMS. The observed products do not include the target compound (tert-butylamino)iodosilane. Instead, the products included SiI(NHtBu)$_3$ and a cyclic [—SiH$_2$N(tBu)-]$_3$. Applicants believe that the H atom on the amino group may lead to undesired polymerized products.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present inven-

What is claimed is:

1. A method of synthesizing an aminohalosilane, the method comprising reacting a halosilane having the formula $Si_aH_bX_c$ with an aminosilane having the formula $Si_dH_e(NR^1R^2)_f$ to produce the aminohalosilane reaction product having the formula:

$Si_wH_xX_y(NR^1R^2)_z$ wherein X=Br or I; each $R^1$ and $R^2$ independently selected from a $C_1$-$C_{10}$ alkyl, aryl, or hetero group; a, d, and w=1 to 4; b+c=2a+2; b=1 to 2a+1; c=1 to 2a+1; e+f=2d+2; e=1 to 2d+1; f=1 to 2d+1; x+y+z=2w+2; x=1 to 2w; y=1 to 2w; z=1 to 2w; and $R^1$ and $R^2$ may be joined to form a nitrogen-containing heterocycle.

2. The method of claim 1, wherein a molar ratio of the halosilane and the aminosilane ranges from approximately 10:1 to 1:10.

3. The method of claim 1, further comprising isolating the aminohalosilane reaction product from a crude product produced by the reaction.

4. The method of claim 1, further comprising distilling the aminohalosilane reaction product.

5. The method of claim 1, further comprising subliming the aminohalosilane reaction product.

6. The method of claim 1, wherein X=I.

7. The method of claim 6, wherein the halosilane is $SiH_2I_2$.

8. The method of claim 1, wherein X=Br.

9. The method of claim 8, wherein the halosilane is $SiH_2Br_2$.

10. The method of claim 1, wherein a=d and b=e.

11. The method of claim 10, wherein the method produces a single aminohalosilane reaction product and no byproducts.

12. The method of claim 1, wherein the reaction is performed in a solvent.

13. The method of claim 1, wherein the reaction does not utilize a solvent.

14. A method of synthesizing an aminohalosilane comprising the steps of:
adding a dibromosilane or diiodosilane to a reactor;
adding an aminosilane having the formula $Si_dH_e(NR^1R^2)_f$ to the reactor to produce a mixture, wherein each $R^1$ and $R^2$ independently selected from a $C_1$-$C_{10}$ alkyl, aryl, or hetero group; d=1 to 4; e+f=2d+2; e=1 to 2d+1; and f=1 to 2d+1;
stirring the mixture to form a stirred mixture; and
isolating the aminohalosilane from the stirred mixture.

15. The method of claim 14, wherein d=1 and e=2.

16. The method of claim 15, wherein the method produces a single aminohalosilane reaction product and no byproducts.

17. The method of claim 14, wherein the reaction is performed in a solvent.

18. The method of claim 14, wherein the reaction does not utilize a solvent.

19. The method of claim 14, further comprising distilling the aminohalosilane reaction product.

20. The method of claim 14, further comprising subliming the aminohalosilane reaction product.

* * * * *